（12）United States Patent
Kang et al.

(10) Patent No.: US 8,977,021 B2
(45) Date of Patent: Mar. 10, 2015

(54) SYSTEMS AND METHODS FOR CUSTOMIZING INTERACTIVE HAPTIC BOUNDARIES

(71) Applicant: MAKO Surgical Corp., Ft. Lauderdale, FL (US)

(72) Inventors: Hyosig Kang, Weston, FL (US); Jason Otto, Plantation, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 182 days.

(21) Appl. No.: 13/725,513

(22) Filed: Dec. 21, 2012

(65) Prior Publication Data

US 2013/0211792 A1    Aug. 15, 2013

Related U.S. Application Data

(60) Provisional application No. 61/581,632, filed on Dec. 30, 2011.

(51) Int. Cl.
*G06F 19/00* (2011.01)
*A61B 19/00* (2006.01)

(52) U.S. Cl.
CPC ............ *G06F 19/3437* (2013.01); *A61B 19/50* (2013.01); *A61B 19/2203* (2013.01); *A61B 2019/2292* (2013.01); *A61B 2019/502* (2013.01); *A61B 2019/505* (2013.01); *A61B 2019/507* (2013.01); *A61B 2019/508* (2013.01)
USPC ...................................................... 382/128

(58) Field of Classification Search
CPC ..... G06T 7/0012; G06T 7/0014; G06T 9/001; G06T 19/003; G06T 2207/30008; G06T 2207/30052; G06T 2219/2004; G06F 19/3437; A61B 19/50; A61B 2019/502; A61B 2019/505; A61B 2019/508
USPC .................... 382/128, 131, 132, 154; 703/11; 623/20.14, 914; 128/898
See application file for complete search history.

(56) References Cited

U.S. PATENT DOCUMENTS

| 2007/0142751 | A1* | 6/2007 | Kang et al. .................... 600/587 |
| 2009/0149977 | A1* | 6/2009 | Schendel ........................ 700/98 |
| 2010/0153081 | A1 | 6/2010 | Bellettre et al. |

FOREIGN PATENT DOCUMENTS

| WO | WO-2006/091494 A1 | 8/2006 |
| WO | WO-2011/041428 A2 | 4/2011 |

OTHER PUBLICATIONS

International Search Report and Written Opinion for International Application No. PCT/US2012/071337, mailed Apr. 19, 2013, 16 pages.

* cited by examiner

*Primary Examiner* — Andrew W Johns
(74) *Attorney, Agent, or Firm* — Foley & Lardner LLP (57) ABSTRACT

A method for customizing an interactive haptic boundary based on a patient-specific feature comprises identifying a reference feature associated with a virtual implant model. The method also comprises determining an intersection between the identified reference feature and a virtual model associated with an anatomy of the patient. A virtual haptic boundary is generated based on the determined intersection between the identified reference feature associated with the virtual implant model and the virtual model associated with the anatomy of the patient.

25 Claims, 8 Drawing Sheets

SYSTEMS AND METHODS FOR CUSTOMIZING INTERACTIVE HAPTIC BOUNDARIES

CROSS-REFERENCE TO RELATED PATENT APPLICATIONS

This application claims the benefit of U.S. Provisional Application No. 61/581,632, filed Dec. 30, 2011, which is incorporated by reference herein in its entirety.

BACKGROUND

The present disclosure relates generally to force feedback systems associated with computer-assisted surgery ("CAS") systems and, more particularly, to systems and methods for customizing interactive haptic boundaries associated with CAS systems based on patient-specific information.

The knee joint comprises the interface between the distal end of the femur and the proximal end of the tibia. In a properly-functioning knee joint, medial and lateral condyles of the femur pivot smoothly along menisci attached to respective medial and lateral condyles of the tibia. When the knee joint is damaged, the natural bones and cartilage that form the joint may be unable to properly articulate, which can lead to joint pain and, in some cases, interfere with normal use of the joint.

In some situations, surgery is required to restore normal use of the joint and reduce pain. Depending upon the severity of the damage, the surgery may involve partially or completely replacing the joint with prosthetic components. During such knee replacement procedures, a surgeon resects damaged portions of the bone and cartilage, while attempting to leave healthy tissue intact. The surgeon then fits the healthy tissue with artificial prosthetic components designed to replicate the resected tissue and restore proper knee joint operation.

Typically, prior to the surgery, the surgeon develops a preliminary ("pre-operative") plan that serves as a guide to performing the surgery. As part of the pre-operative planning, the surgeon surveys, among other things, the size, shape, kinematic function, and condition of the patient's joint. Using computer-assisted surgery systems, this survey can be performed by obtaining computer-based images of the joint and generating a computer-based model of the joint of the patient in virtual software space. Using this virtual model, the surgeon can evaluate the condition of the anatomical features of the joint and plan, among other things, the location and amount of bone that needs to be removed and the position and orientation in which the prosthetic components should be implanted on the bone to restore normal joint functionality.

Although the surgeon has a great degree of flexibility in customizing most aspects of the surgery based on the unique anatomy of the patient, the surgeon is typically limited to selecting from among a fairly small number of different prosthetic implant components. In many situations, a surgeon performs surgery on a patient whose anatomy does not precisely match any of the available prosthetic implant components. As a result, the surgeon may be required to select the prosthetic implant that most closely fits—but does not precisely match—the patient's anatomy. The surgeon can then modify the surgical plan (either pre or intra-operatively) to accommodate for the selected prosthetic components.

In some situations, the CAS system may include a force feedback control system that is coupled to one or more surgical instruments (e.g., cutting tools) and configured to provide force feedback for controlling the surgical instrument during the surgery. The force feedback control system may constrain the cutting tool to limit the position or operation of the surgical instrument to within certain predefined boundaries. By allowing users to strategically define the placement of the virtual boundaries associated with the force feedback control system, these CAS systems enable surgeons to precisely and accurately control the resection and sculpting of the bone in preparation for receiving the prosthetic implant.

Because CAS systems provide a solution for accurately, reliably, and precisely executing bone cuts by defining the boundaries at which a cutting surface of a surgical instrument can operate, some CAS systems now include virtual software models that match the size and shape of available prosthetic implants. The virtual software model of the implant(s) can be positioned (in software) relative to the virtual model(s) of the patient's joint prior to or during the surgical procedure. Once positioned, the software model of the implant may be "registered" to the virtual model of the patient's anatomy so that the cutting surface is constrained to operate only within the area defined by the software model of the implant, limiting tissue removal only to the specific area of the patient's bone associated with the registered placement of the implant.

Although systems that provide virtual models (and corresponding haptic boundaries) associated with a selection of available implants allow surgeons to quickly and efficiently define a resection pattern for preparing the bone to receive the implant, they may nonetheless have limitations that make them less than optimal. Specifically, each virtual implant model is associated with a corresponding fixed haptic boundary, which may be limited in size and shape to the geometry associated with the virtual implant model. This may be particularly problematic in situations in which the surgeon is forced to select an undersized prosthetic implant, but nonetheless wishes to remove areas of diseased or damaged tissue that may be located beyond the boundaries required to accommodate the undersized prosthetic implant.

The presently disclosed systems and methods for customizing interactive haptic boundaries are directed to overcoming one or more of the problems set forth above and/or other problems in the art.

SUMMARY

In accordance with one aspect, the present disclosure is directed to a method for customizing an interactive haptic boundary based on a patient-specific feature. The method may comprise identifying a reference feature associated with a virtual implant model. The method may also comprise determining an intersection between the identified reference feature and a virtual model associated with an anatomy of the patient. A virtual haptic boundary may be generated based on the determined intersection between the identified reference feature associated with the virtual implant model and the virtual model associated with the anatomy of the patient.

According to another aspect, the present disclosure is directed to another method for customizing an interactive haptic boundary based on a patient-specific feature. The method may comprise displaying a graphical representation of an implant in virtual coordinate space and displaying a graphical representation of a bone in virtual coordinate space. The method may further comprise positioning the graphical representation of the implant relative to the graphical representation of the bone based on a user input. The method may also comprise extracting reference feature information associated with the virtual representation of the implant, and mapping the extracted reference feature information to the graphical representation of the bone. Information indicative of a positional landmark associated with the bone may be received. An intersection between the positional landmark and the mapped reference feature may be estimated, and a virtual haptic boundary may be generated based, at least in part, on the estimated intersection between the positional landmark and the mapped reference feature.

In accordance with yet another aspect, the present disclosure is directed to a computer-assisted surgery system comprising a display, an input device configured to receive data input by a user, and a processor, operatively coupled to the input device and the display. The processor may be configured to identify a reference feature associated with a virtual implant model, and determine an intersection between the identified reference feature and a virtual model associated with an anatomy of the patient. The processor may also be configured to generate a virtual haptic boundary based on the determined intersection between the identified reference feature associated with the virtual implant model and the virtual model associated with the anatomy of the patient. The processor may also be configured to display the generated virtual haptic boundary and the virtual model associated with the anatomy of the patient on the display.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE FIGURES

The accompanying drawings, which are incorporated in and constitute a part of this specification, illustrate several embodiments that, together with the description, serve to explain the principles and features of the present disclosure.

DETAILED DESCRIPTION

Reference will now be made in detail to exemplary embodiments of the present disclosure, examples of which are illustrated in the accompanying drawings. Wherever possible, the same reference numbers will be used throughout the drawings to refer to the same or similar parts.

A healthy knee joint comprises the interface between the distal end of the femur and the proximal end of the tibia. If the healthy knee joint becomes damaged due, for example, to injury or disease, knee surgery may be required to restore normal structure and function of the joint. If the damage to the knee is severe, total knee arthroplasty ("TKA") may be required. TKA typically involves the removal of the damaged portion of joint and the replacement of the damaged portion of the joint with one or more prosthetic components.

In some TKA procedures, one or more of cruciate ligaments (including anterior cruciate ligament and/or posterior cruciate ligament) may be left intact, to be re-used with the prosthetic implants to form the new knee joint. In these "cruciate-retaining" applications, the prosthetic implant components may be configured to avoid interference with or impingement on the retained cruciate ligaments passing through the intercondylar area of the knee joint. For example, each of the femoral and tibial prosthetic components may be designed with a intercondylar "notch" that extends from the posterior of the prosthetic component toward the anterior of the prosthetic component. The femoral and tibial intercondylar notches overlap in the vertical direction, providing a passage that allows the cruciate ligament to pass from the femoral intercondylar fossa down to the tibial eminence.

Figure 1:
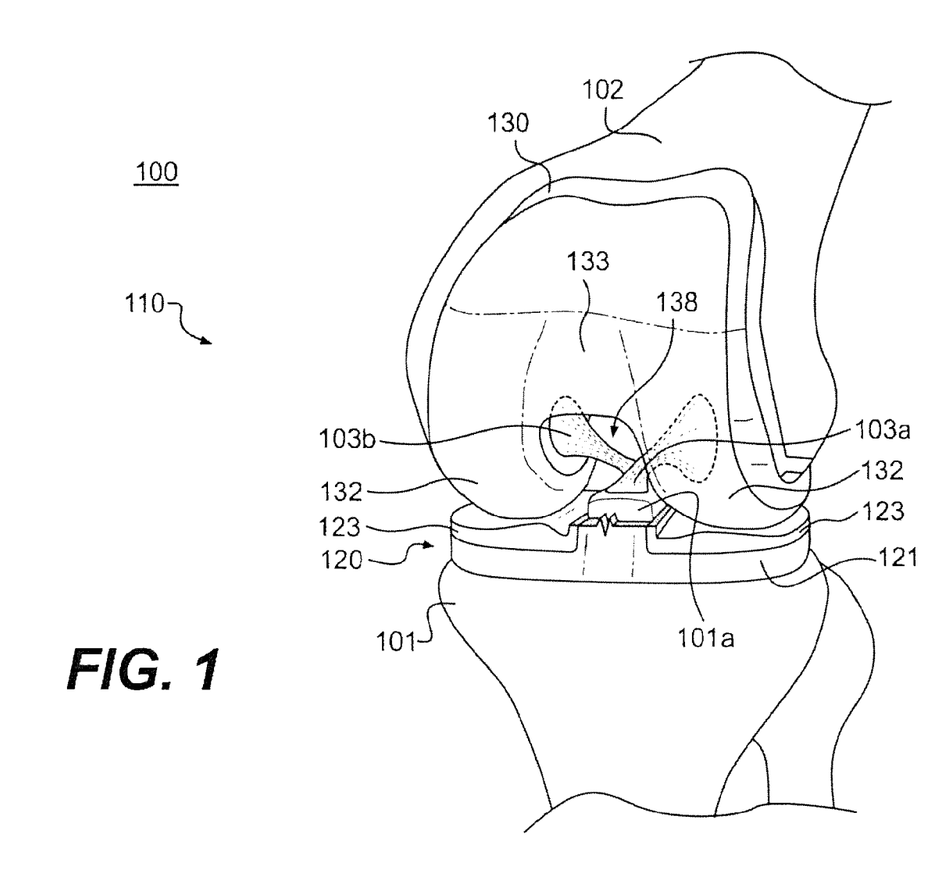
FIG. 1 illustrates a perspective view of post-operative prosthetic knee joint fitted with a cruciate-retaining prosthetic system, consistent with certain disclosed embodiments.

Because cruciate ligaments are exposed to significant tensile force during normal knee joint use, it is important that the attachment sites where the cruciate ligaments attach to the femur and tibia have sufficient strength to properly anchor the cruciate ligaments to the bone. Otherwise, the force applied by the cruciate ligament strains the tissue around the attachment site, possibly leading to failure of the joint, which may require corrective surgery to repair. One way to limit the possibility of such a failure is to limit the amount of bone resected at or near the attachment site(s) (i.e., the intercondylar fossa of the femur and tibial emmence 101a of the tibia). Limiting the amount of disturbance of native tissue at the attachment sites helps preserve the natural anchoring mechanism of the tissue, which decreases the likelihood of failure at the attachment site. As will be explained in greater detail below, prosthetic systems consistent with the presently disclosed embodiments may limit the amount of bone resection that is required for a TKA procedure. FIG. 1 illustrates a perspective view of a knee joint 100 fitted with a prosthetic implant system 110 having a tibial implant system 120 that is configured to limit the amount of bone resection that is required at the surface of tibia 101.

In the embodiment illustrated in FIG. 1, prosthetic implant system 110 may comprise a plurality of components, each of which is configured to replace a resected portion of a native knee joint. According to one embodiment, prosthetic implant system 110 may include a tibial implant system 120 configured to replace a resected portion of a native tibia 101. Prosthetic implant system 110 may also include a femoral component 130 configured to replace a resected portion of a native femur 102. After implantation during knee replacement surgery, tibial implant system 120 and femoral component 130 cooperate to replicate the form and function of the native knee joint.

Femoral component 130 may be secured to the distal end of femur 102 and configured to replace the structure and function of the native femoral portion of knee joint 100. As such, femoral component 130 may be manufactured from surgical-grade metal or metal alloy material (such as surgical-grade steel, titanium or titanium allow, a cobalt-chromium alloy, a zirconium alloy, or tantalum) that is substantially rigid for providing sufficient strength to support the forces required of the knee joint. According to one embodiment, femoral component 130 may embody a single component having a plurality of different structural features, each configured to perform a particular function associated with the knee joint 100. For example, femoral component 130 may comprise a pair of condyles 132, each of which is coupled to a patellar guide portion 133. The pair of condyles 132 may be separated from one another by an intercondylar notch 138, which provides a channel through which one or more cruciate ligaments 103, such as anterior cruciate ligament (ACL) 103a and/or posterior cruciate ligament (PCL) 103b, may pass.

Tibial implant system 120 may include a plurality of components that cooperate to provide a stable surface that articulates with femoral component 130 to restore proper knee joint function. As illustrated in FIG. 1, tibial implant system 120 may include a base portion 121 and one or more insert portions 123. During a knee replacement procedure, base portion 121 may be secured to the proximal end of the tibia 101, which has been surgically prepared by removing damaged bone and tissue and reshaping the healthy bone to receive the base portion 121. Once base portion 121 is secured to tibia 101, the surgeon completes assembly of tibial implant system 120 by engaging and securing insert portions 123 within base portion 121. Base portion 121 of tibial prosthetic system may be configured with a passage through the center to allow for connection between the retained cruciate ligaments 103 and tibial eminence 101a.

Base portion 121 may be configured to emulate the structure and function of the top surface of tibia 101. Thus, similar to femoral component 130, base portion 110 may be manufactured from surgical-grade metal or metal alloy material (such as surgical-grade steel, titanium or titanium allow, a cobalt-chromium alloy, a zirconium alloy, or tantalum) that is substantially rigid for providing a stable base upon which to reconstruct the remainder of the prosthetic joint Insert portions 123 may be designed to emulate the form and function of certain components of the natural femorotibial interface, including, among other things, medial and lateral menisci of the knee joint. As such, insert portions 123 may be constructed of smooth, semi-rigid synthetic or semi-synthetic plastic, rubber, or polymer material. Insert portions 123 may be configured to provide a smooth surface that is designed to articulate with a femoral component 130 during normal knee operation. According to one embodiment, insert portions 123 are configured to removably engage with base portion 121. Accordingly, insert portions 123 are configured for periodic replacement if insert portions 123 deteriorate over time due, for example, to excessive wear.

In order to ensure precise and accurate preparation of the joint to receive a prosthetic implant, CAS system may be used to generate a graphical representation of the surgical site and a corresponding virtual guide that may aid the surgeon in properly aligning the tool prior to interaction with patient's anatomy. Many CAS systems include software that allows users to electronically register certain anatomic features (e.g., bones, soft tissues, etc.), surgical instruments, and other landmarks associated with the surgical site. CAS systems may generate a graphical representation of the surgical site based on the registration of the anatomic features. The CAS software also allows users to plan certain aspects of the surgical procedure, and register these aspects for display with the graphical representation of the surgical site. For example, in a knee joint replacement procedure, a surgeon may register target navigation points, the location and depth of bone and tissue cuts, virtual boundaries that may be associated with a corresponding reference for the application of haptic force, and other aspects of the surgery.

Figure 2:
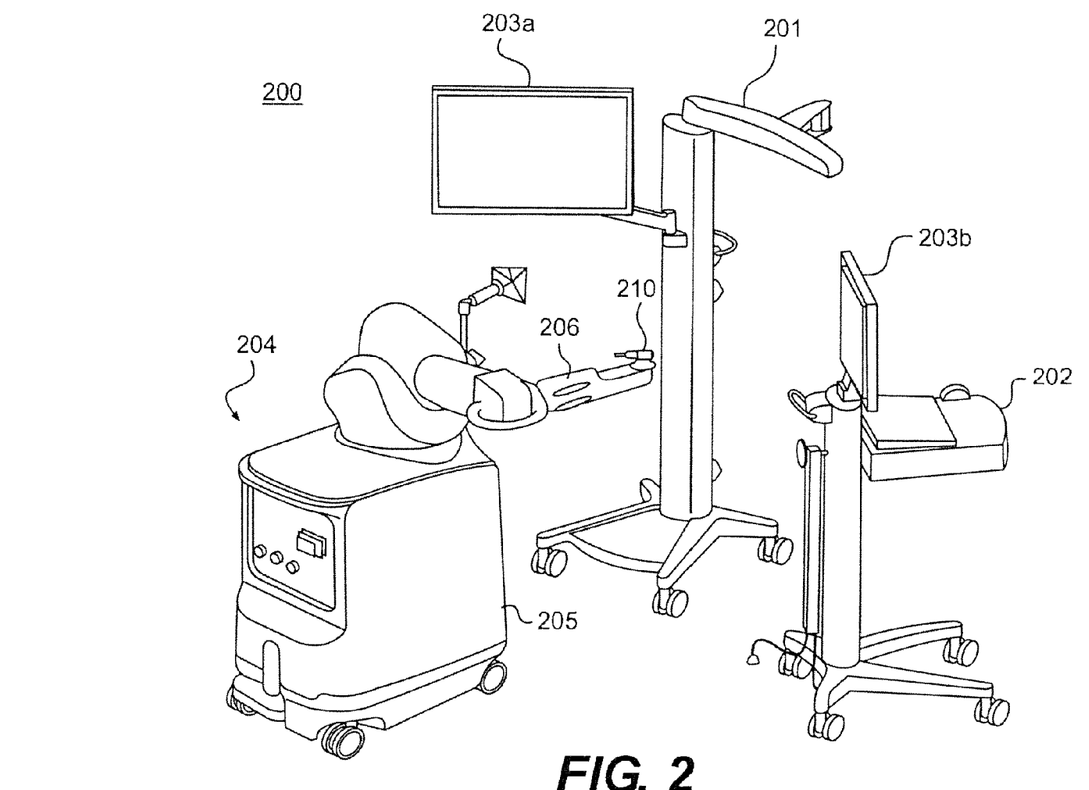
FIG. 2 provides a schematic illustration of an exemplary computer-assisted surgery (CAS) system, in which certain methods consistent with the disclosed embodiments may be implemented.

FIG. 2 provides a schematic diagram of an exemplary computer-assisted surgery (CAS) system 200, in which processes and features associated with certain disclosed embodiments may be implemented. CAS system 200 may be configured to perform a wide variety of orthopedic surgical procedures such as, for example, partial or total joint replacement surgeries. As illustrated in FIG. 2, CAS system 200 may comprise a tracking system 201, computer-assisted navigation system 202, one or more display devices 203a, 203b, and a robotic arm 204. It should be appreciated that CAS system 200, as well as the methods and processes described herein, may be applicable to many different types of joint replacement procedures. Although certain disclosed embodiments may be described with respect to knee replacement procedures, the concepts and methods described herein may be applicable to other types of orthopedic surgeries, such as partial hip replacement, full or partial hip resurfacing, shoulder replacement or resurfacing procedures, and other types of orthopedic procedures.

Robotic arm 204 can be used in an interactive manner by a surgeon to perform a surgical procedure, such as a knee replacement procedure, on a patient. As shown in FIG. 2, robotic arm 204 includes a base 205, an articulated arm 206, a force system (not shown), and a controller (not shown). A surgical tool 210 (e.g., an end effector having an operating member, such as a saw, reamer, or burr) may be coupled to the articulated arm 206. The surgeon can manipulate the surgical tool 210 by grasping and manually moving the articulated arm 206 and/or the surgical tool 210.

The force system and controller are configured to provide control or guidance to the surgeon during manipulation of the surgical tool. The force system is configured to provide at least some force to the surgical tool via the articulated arm 206, and the controller is programmed to generate control signals for controlling the force system. In one embodiment, the force system includes actuators and a backdriveable transmission that provide haptic (or force) feedback to constrain or inhibit the surgeon from manually moving the surgical tool beyond predefined virtual boundaries defined by haptic objects as described, for example, in U.S. Pat. No. 8,010,180 and/or U.S. patent application Ser. No. 12/654,519 (U.S. Patent Application Pub. No. 2010/0170362), filed Dec. 22, 2009, each of which is hereby incorporated by reference herein in its entirety. According to one embodiment, CAS system 200 is the RIO® Robotic Arm Interactive Orthopedic System manufactured by MAKO Surgical Corp. of Fort Lauderdale, Fla. The force system and controller may be housed within the robotic arm 204.

Tracking system 201 may include any suitable device or system configured to track the relative locations, positions, orientations, and/or poses of the surgical tool 210 (coupled to robotic am 204) and/or positions of registered portions of a patient's anatomy, such as bones. Such devices may employ optical, mechanical, or electromagnetic pose tracking technologies. According to one embodiment, tracking system 201 may comprise a vision-based pose tracking technology, wherein an optical detector, such as a camera or infrared sensor, is configured to determine the position of one or more optical transponders (not shown). Based on the position of the optical transponders, tracking system 201 may capture the pose (i.e., the position and orientation) information of a portion of the patient's anatomy that is registered to that transponder or set of transponders.

Navigation system 202 may be communicatively coupled to tracking system 201 and may be configured to receive tracking data from tracking system 201. Based on the received tracking data, navigation system 202 may determine the position and orientation associated with one or more registered features of the surgical environment, such as surgical tool 210 or portions of the patient's anatomy. Navigation system 202 may also include surgical planning and surgical assistance software that may be used by a surgeon or surgical support staff during the surgical procedure. For example, during a joint replacement procedure, navigation system 202 may display images related to the surgical procedure on one or both of the display devices 203a, 203b.

Figure 3:
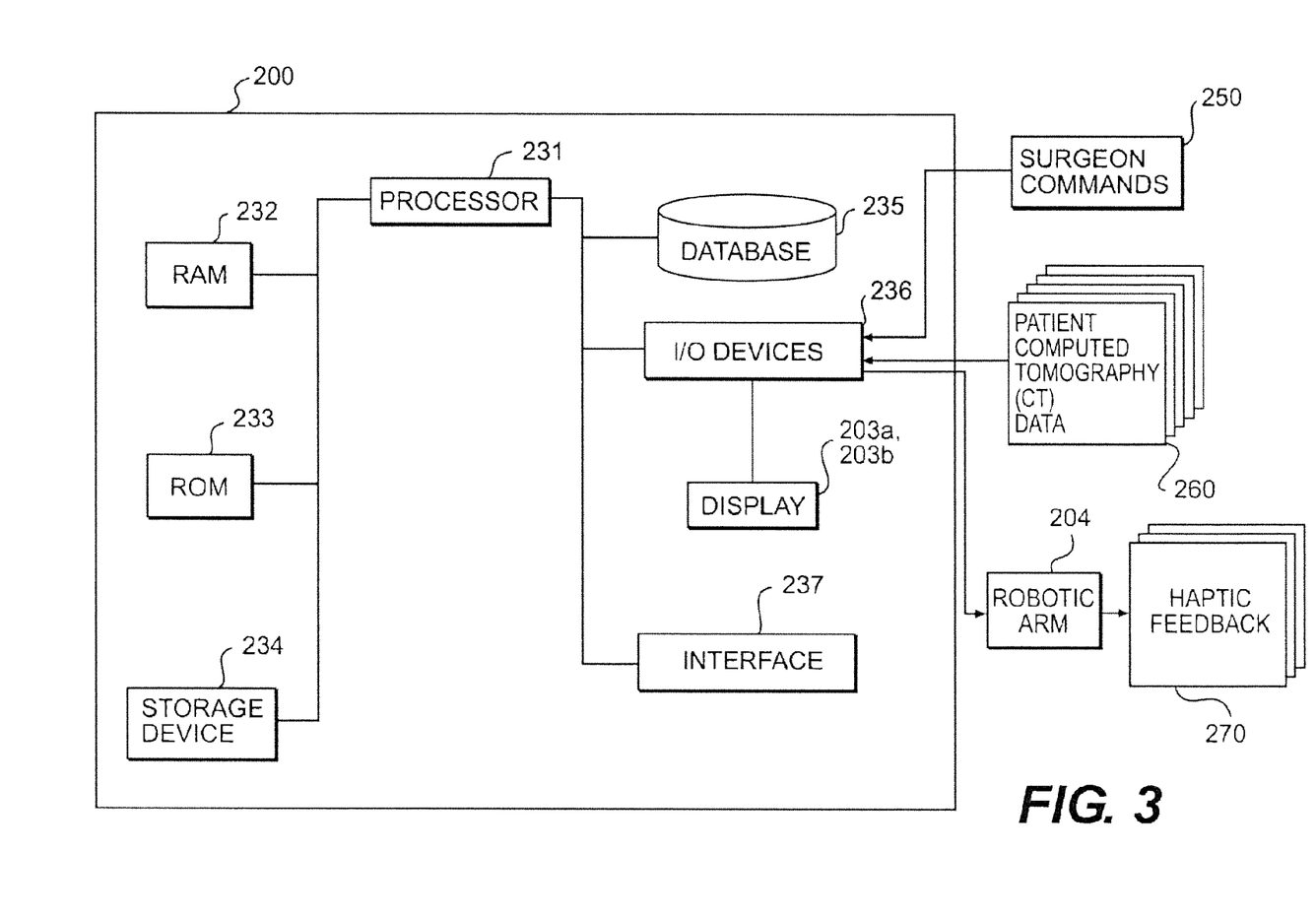
FIG. 3 provides a schematic diagram of an exemplary computer system, which may be used in one or more components associated with the CAS system illustrated in FIG. 2.

Navigation system 202 (and/or one or more constituent components of CAS system 200) may include or embody a processor-based system (such as a general or special-purpose computer) in which processes and methods consistent with the disclosed embodiments may be implemented. For example, as illustrated in FIG. 3, CAS system 200 may include one or more hardware and/or software components configured to execute software programs, such as, tracking software, surgical navigation software, 3-D bone modeling or imaging software, and/or software for establishing and modifying virtual haptic boundaries for use with a force system to provide haptic feedback to surgical tool 210. For example, CAS system 200 may include one or more hardware components such as, for example, a central processing unit (CPU) (processor 231); computer-readable media, such as a random access memory (RAM) module 232, a read-only memory (ROM) module 233, and a storage device 234; a database 235; one or more input/output (I/O) devices 236; and a network interface 237. The computer system associated with CAS system 200 may include additional, fewer, and/or different components than those listed above. It is understood that the components listed above are exemplary only and not intended to be limiting.

Processor 231 may include one or more microprocessors, each configured to execute instructions and process data to perform one or more functions associated with CAS system 200. As illustrated in FIG. 3, processor 231 may be communicatively coupled to RAM 232, ROM 233, storage device 234, database 235, I/O devices 236, and network interface 237. Processor 231 may be configured to execute sequences of computer program instructions to perform various processes, which will be described in detail below. The computer program instructions may be loaded into RAM for execution by processor 231.

Computer-readable media, such as RAM 232, ROM 233, and storage device 234, may be configured to store computer-readable instructions that, when executed by processor 231, may cause CAS system 200 or one or more constituent components, such as navigation system 202, to perform functions or tasks associated with CAS system 200. For example, computer readable media may include instructions for causing the CAS system 200 to perform one or more methods for determining changes in parameters of a hip joint after a hip arthroplasty procedure. Computer-readable media may also contain instructions that cause tracking system 201 to capture positions of a plurality of anatomical landmarks associated with certain registered objects, such as surgical tool 210 or portions of a patient's anatomy, and cause navigation system 202 to generate virtual representations of the registered objects for display on I/O devices 236. Exemplary methods for which computer-readable media may contain instructions will be described in greater detail below. It is contemplated that each portion of a method described herein may have corresponding instructions stored in computer-readable media for causing one or more components of CAS system 200 to perform the method described.

I/O devices 236 may include one or more components configured to communicate information with a user associated with CAS system 200. For example, I/O devices 236 may include a console with an integrated keyboard and mouse to allow a user (e.g., a surgeon) to input parameters (e.g., surgeon commands 250) associated with CAS system 200. I/O devices 236 may also include a display, such as monitors 203a, 203b, including a graphical user interface (GUI) for outputting information on a monitor. I/O devices 236 may also include peripheral devices such as, for example, a printer for printing information associated with CAS system 200, a user-accessible disk drive (e.g., a USB port, a floppy, CD-ROM, or DVD-ROM drive, etc.) to allow a user to input data stored on a portable media device, a microphone, a speaker system, or any other suitable type of interface device. For example, I/O devices 236 may include an electronic interface that allows a user to input patient computed tomography (CT) data 260 into CAS system 200. This CT data may then be used to generate and manipulate virtual representations of portions of the patient's anatomy (e.g., a virtual model of a tibia 101) in software.

Software associated with CAS system 200 may be configured to enable surgical planning, navigation, and basic image guided surgery capabilities. For example, as is well known, software associated with CAS system 200 may include computer-implemented processes for generating and displaying images (either captured images or computer-generated captured images) from image data sets, computer-implemented processes for determining a position of a tip and an orientation of an axis of a surgical instrument, and computer-implemented processes for registering a patient and an image data set to a coordinate frame of the tracking system 201. These processes may enable, for example, the CAS system 200 to display on the display device(s) 203a, 203b a virtual representation of a tracked surgical instrument (and/or a prosthetic implant) overlaid on one or more images of a patient's anatomy and to update the virtual representation of the tracked instrument in real-time during a surgical procedure. Images generated from the image data set may be two-dimensional or, in the case of a three-dimensional image data set, a three-dimensional reconstruction based, for example, on segmentation of the image data set. According to one embodiment, images associated with the image data set may include CT scan data associated with a patient's anatomy, a prosthetic implant, or any object. When more than one image is shown on the display device(s) 203a, 203b, the CAS system 200 may coordinate the representation of the tracked instrument among the different images.

According to another embodiment, an imageless system may be utilized to generate and manipulate virtual representations of portions of the patient's anatomy (e.g., a virtual model of a tibia 101) in software. Imageless systems include technologies that are well-known in the art, such as systems utilizing statistically shaped models and methods of bone morphing. In one form of imageless system, a virtual representation of a portion of the patient's anatomy is created based on patient-specific characteristics (such as anatomical landmarks obtained by physically touching the patient's anatomy using a probe tool). In other imageless systems, a three-dimensional virtual representation of a portion of the patient's anatomy is obtained by selecting a three-dimensional model from a database or library of bone models. The selected bone model can then be deformed based on patient-specific characteristics, creating a three-dimensional representation of the patient's anatomy.

Processor 231 associated with CAS system 200 may be configured to establish a virtual haptic geometry associated with or relative to one or more features of a patient's anatomy. As explained, CAS system 200 may be configured to create a virtual representation of a surgical site that includes, for example, virtual representations of a patient's anatomy, a surgical instrument to be used during a surgical procedure, a probe tool for registering other objects within the surgical site, and any other such object associated with a surgical site.

In addition to physical objects, CAS system 200 may be configured to generate virtual objects that exist in software and may be useful during the performance of a surgical procedure. For example, CAS system 200 may be configured to generate virtual boundaries that correspond to a surgeon's plan for preparing a bone, such as boundaries defining areas of the bone that the surgeon plans to cut, remove, or otherwise alter. Alternatively or additionally, CAS system 200 may define virtual objects that correspond to a desired path or course over which a portion of surgical tool 210 should navigate to perform a particular task.

Virtual boundaries and other virtual objects may define a point, line, or surface within a virtual coordinate space (typically defined relative to an anatomy of a patient) that serves as a boundary at which haptic feedback is provided to a surgical instrument when the tracked position of the surgical instrument interacts with the virtual boundary or object. For example, as the surgeon performs a bone cutting operation, tracking system 201 of CAS system 200 tracks the location of the cutting tool and, in most cases, allows the surgeon to freely move the tool in the workspace. However, when the tool is in proximity to a virtual haptic boundary (that has been registered to the anatomy of the patient), CAS system 200 controls the force feedback system to provide haptic guidance that tends to constrain the surgeon from penetrating the virtual haptic boundary with the cutting tool. For example, a virtual haptic boundary may be associated with the geometry of a virtual model of a prosthetic implant, and the haptic guidance may comprise a force and/or torque that is mapped to the virtual boundary and experienced by the surgeon as resistance to constrain tool movement from penetrating the virtual boundary. Thus, the surgeon may feel as if the cutting tool has encountered a physical object, such as a wall. In this manner, the virtual boundary functions as a virtual cutting guide. Accordingly, the force feedback system of CAS system 200 communicates information to the surgeon regarding the location of the tool relative to the virtual boundary, and provides physical force feedback to guide the cutting tool during the actual cutting process. The force feedback system of CAS system 200 may also be configured to limit the user's ability to manipulate the surgical tool.

Figure 4:
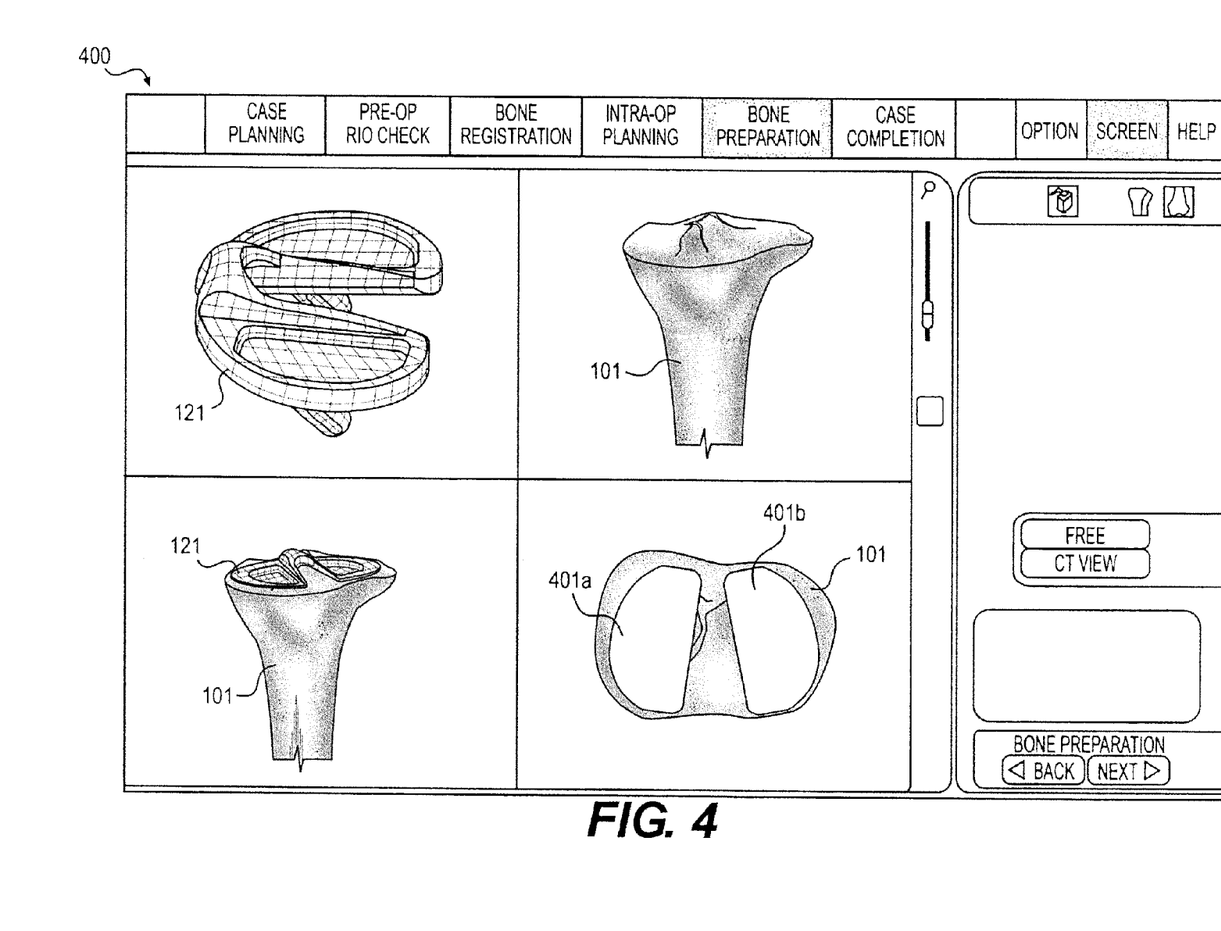
FIG. 4 illustrates an exemplary screen shot associated with a graphical user interface of the CAS system, in accordance with certain disclosed embodiments.
Figure 5:
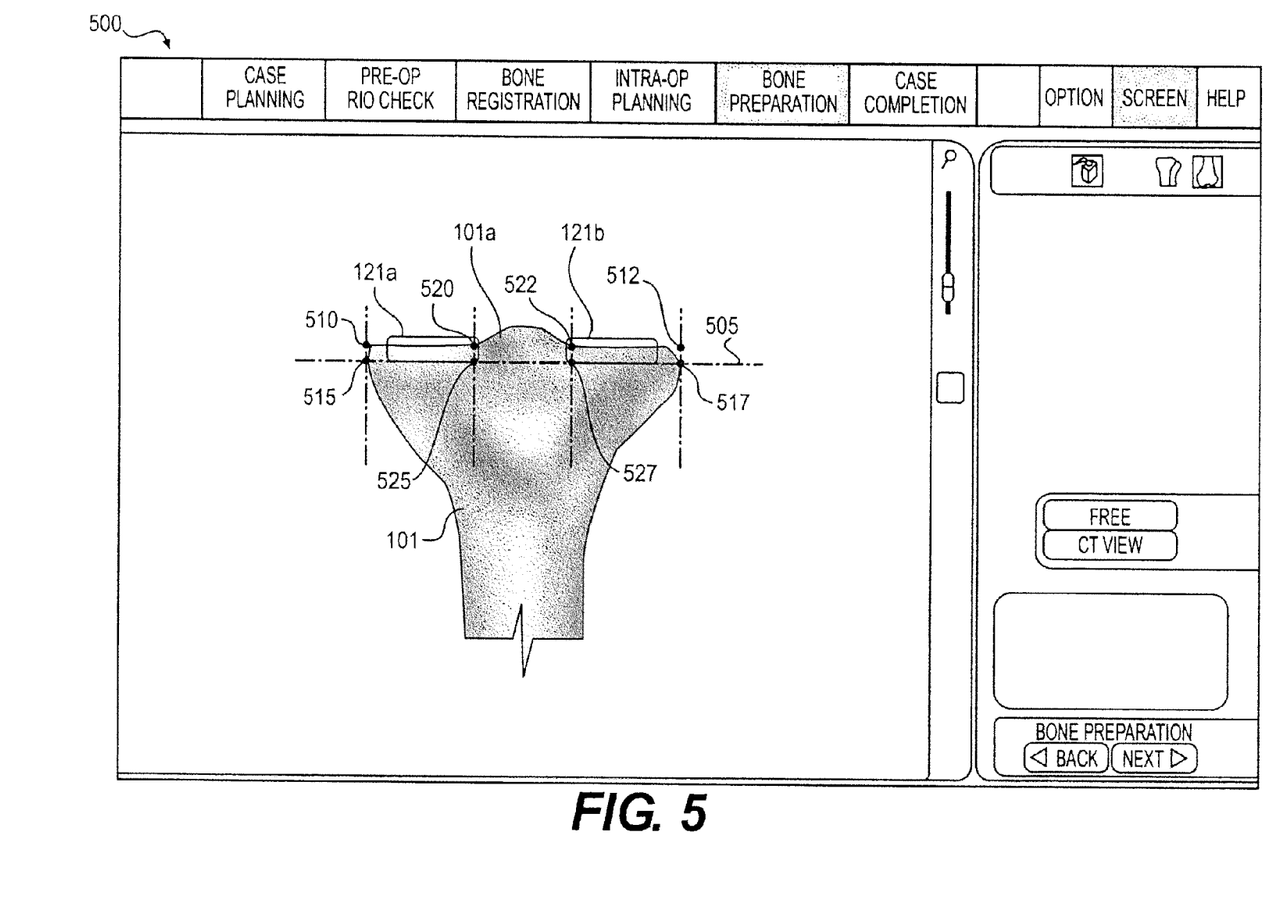
FIG. 5 illustrates another exemplary screen shot associated with a graphical user interface of CAS system, in accordance with the disclosed embodiments.

Systems and methods consistent with the disclosed embodiments provide a solution for customizing a virtual haptic boundary and providing a haptic feedback for guiding the surgical instrument. According to one embodiment, the virtual haptic boundary may be customized based on a user request to modify a default boundary associated with a corresponding implant geometry. Alternatively or additionally, the virtual haptic boundary may be customized based, at least in part, on a detection of the patient's anatomy (e.g., a location of soft tissue, the edge perimeter of a bone, etc.). The process for customizing the virtual haptic boundary may be part of an implant planning phase, during which the surgeon pre-operatively or intra-operatively plans the placement of prosthetic implants and the corresponding modification/removal of joint tissue to accommodate the implant. FIGS. 4 and 5 provide exemplary screen shots of a graphical user interface associated with planning software for CAS system 200.

FIG. 4 illustrates an exemplary screen shot 400 associated with a graphical user interface screen of planning software associated with CAS system 200. As illustrated in FIG. 4, planning software may include virtual models of prosthetic implants, such as a tibial base portion 121 associated with tibial implant system 120. According to one embodiment, a virtual implant model may be provided by the manufacturer of the prosthetic implant and may provide a graphical representation of the geometry of the prosthetic implant. Using the graphical representation of the geometry, a virtual haptic boundary may be created and associated with the virtual implant model.

The graphical user interface 400 may include a plurality of sub-screens, each of which is configured to display a particular feature of the implant planning For example, graphical user interface 400 may include a first sub-screen (e.g., upper left) for displaying the selected virtual implant model (e.g., a model associated with tibia base portion 121). Graphical user interface 400 may include a second sub-screen (upper right) for displaying the virtual model associated with the patient's anatomy (e.g., tibia 101) upon which the implant will be positioned. Graphical user interface 400 may include a third sub-screen (lower left) for displaying the planned placement of virtual implant model within the patient's anatomy. Graphical user interface 400 may also include a fourth sub-screen (lower right) for displaying a view of respective medial and lateral resection portions 401*a*, 401*b* associated with the planned implant placement. It is contemplated that the number and view of sub-screens may differ from those provided in the exemplary embodiment illustrated in FIG. 4. It is also contemplated that one or more of the sub-screens allow a user to interactively update the view and/or the components within the view. For example, although the lower right screen shows a top view of the simulated resection of the patient's tibia 101 based on the planned implant placement shown in the lower left sub-screen, it is contemplated that the user can select different views (e.g., front, back, side, bottom, etc.) for displaying the contents of the sub-screen.

FIG. 5 provides an alternative embodiment of a graphical user interface 500 associated with planning software of CAS system 200. According to the embodiment shown in FIG. 5, graphical user interface 500 embodies an interactive interface that allows the user to manipulate the position of a prosthetic implant and/or a virtual haptic boundary associated therewith. For example, FIG. 5 provides a rear-view of a virtual model associated with tibial base portion 121 (including medial implant portions 121*a* and lateral implant portion 121*b*), which has been positioned atop a virtual model of the patient's tibia 101.

Graphical user interface 500 may also display a reference feature 505 associated with the virtual implant model. As illustrated in FIG. 5, reference feature 505 may correspond with the plane defined by the bottom surfaces of medial and lateral base portions 121*a*, 121*b*. It is contemplated, however, that reference feature 505 may include or embody any feature (e.g., point, line, or surface) of virtual implant model that defines a reference to which modifications will be made to the virtual haptic boundary.

Using graphical user interface 500, users can modify the virtual haptic boundary that is used for virtually guiding a cutting tool to prepare the bone for placement of a prosthetic implant. For example, a preliminary virtual haptic boundary may be associated with the virtual implant model and designed to substantially match the geometry associated with the virtual implant (e.g., medial and lateral base portions 121*a*, 121*b*). This preliminary virtual haptic boundary may be stretched or contracted to, for example, accommodate certain anatomic feature(s) associated with the patient's anatomy.

To modify the preliminary virtual haptic boundary, the user may identify one or more anatomical features associated with the patient's anatomy. For example, a surgeon may wish to stretch outer edges of virtual haptic boundaries associated with medial and lateral base portions 121a, 121b to allow bone resection to the outer perimeter of the patient's tibia 101. As such, a user may select (or planning software may detect) points 510, 512 associated with the perimeter of tibia 101. The planning software may stretch the outer edges of the preliminary virtual haptic boundaries of medial and lateral base portions 121a, 121b to points 510, 512, respectively. As will be explained in greater detail below, planning software associated with CAS system 200 may identify the intersecting or overlapping areas between the stretched boundary and the patient's anatomy and establish a new, modified virtual haptic boundary based on the extent of the overlapping area(s).

In addition to stretching the virtual haptic boundary, planning software associated with CAS system may also be configured to contract the preliminary virtual boundary to avoid certain sensitive anatomical features. For example, a surgeon may wish to contract the inner edges of virtual haptic boundaries associated with medial and lateral base portions 121a, 121b to limit the operation of the cutting tool near the tibial eminence 101a, and avoid the possibility of inadvertently damaging soft tissues (e.g., ACL or PCL) that attach thereto. The surgeon may use other cutting tools and/or methods to carefully and manually prepare such critical areas.

As shown in FIG. 5, in order to avoid the area surrounding tibial eminence 101a, the user may establish anatomic landmarks 520, 522 corresponding to the inner edges of medial and lateral base portions 121a, 121b, respectively. The planning software may contract the inner edges of the preliminary virtual haptic boundaries of medial and lateral base portions 121a, 121b to points 520, 522, respectively. As will be explained in greater detail below, planning software associated with CAS system 200 may identify the intersecting or overlapping areas between the contracted boundary and the patient's anatomy and establish a new, modified virtual haptic boundary based on the extent of the overlapping area(s).

Figure 6:
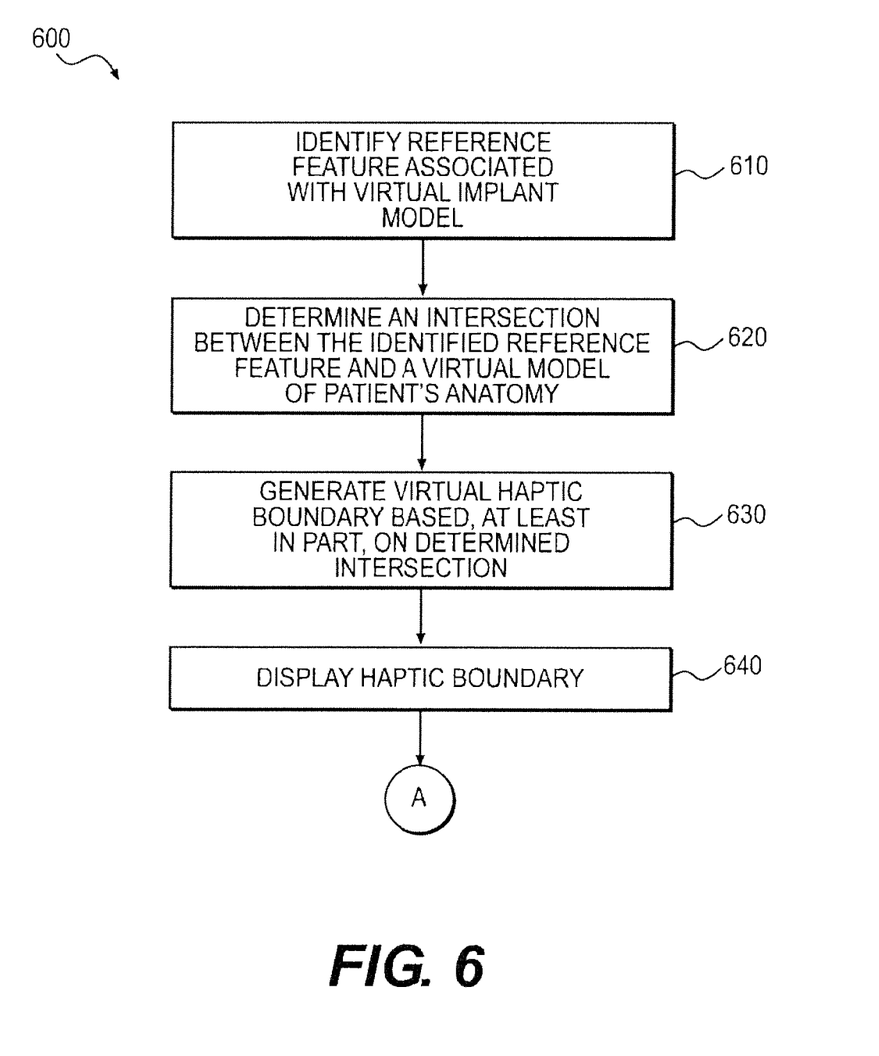
FIG. 6 provides a flowchart illustrating an exemplary method for generating interactive haptic boundaries based on patient-specific anatomic data.

FIG. 6 provides a flowchart 600 that illustrates an exemplary method for generating a patient-specific virtual haptic boundary. According to one embodiment, the method illustrated in FIG. 6 may be implemented during an implant placement planning stage associated with the performance of a surgical procedure. The planning stage may be performed pre-operatively by a surgeon or other medical professional, prior to commencement of the surgical procedure. Alternatively or additionally, the planning stage may be performed (or repeated) intra-operatively, during the medical procedure.

During the implant planning stage, a surgeon or medical professional may use planning software associated with CAS system 200 to plan the placement of prosthetic implants onto or within a patient's anatomy. As such, virtual (i.e., software) 3-D models of prosthetic implants, the patient's anatomy, a surgical instrument (such as cutting tool(s)), and any other physical object that may be used during the surgical procedure may be generated and registered to a virtual coordinate space (generally one that corresponds with the patient's anatomy). Using planning software, the surgeon can virtually position a prosthetic implant relative to the patient's anatomy. Once the placement has been finalized, the surgeon can then register one or more reference features associated with virtual implant to the patient's anatomy to provide the surgeon with a graphical view to show how the patient's anatomy can be modified to accommodate the planned placement of the implant.

As illustrated in flowchart 600 of FIG. 6, once the implant has been placed in a desired position relative to the patient's anatomy, the method may commence by identifying the position and orientation of a reference feature associated with the virtual implant model in the virtual coordinate space (Step 610). The reference feature of the virtual implant model may embody one or more points, lines, planes, or surfaces of the virtual implant model and, by extension, the prosthetic model associated therewith. As illustrated in the embodiment illustrated in FIG. 5, the reference feature may be a reference plane 505 defined by the bottom surfaces of medial and lateral base portions 121a, 121b tibial implant system 120. Alternatively or additionally, the reference feature may include or embody any feature associated with the implant that the surgeon wishes to use as the reference with which to customize virtual haptic boundaries.

Once the reference feature associated with the virtual implant model has been established, an intersection between the identified reference feature and virtual model of the patient's anatomy may be determined (Step 620). For example, as illustrated in FIG. 5, planning software associated with CAS system 200 may be configured to determine areas where the surfaces of medial base portion 121a and lateral base portion 121b intersect and/or overlap the virtual model of the patient's tibia 101. According to one embodiment, processor 231 of CAS system 200 may be configured to calculate, based on the position of virtual implant model relative to the virtual model associated with the patient's anatomy, the overlapping volume between the virtual implant model and the virtual model of the patient's anatomy.

Upon identifying the overlapping volume between the virtual implant model and the virtual model of the patient's anatomy, planning software of CAS system 200 may be configured to generate a preliminary virtual haptic boundary based, at least in part, on the determined intersection between the virtual implant model and the patient-specific anatomic model (Step 630). This preliminary virtual haptic boundary typically corresponds closely with the geometric shape of the prosthetic implant. According to one embodiment, however, it may differ slightly from the geometry of the implant. For example, the preliminary virtual haptic boundary may be slightly larger than the prosthetic implant to allow sufficient space for surgical tool access (e.g., to accommodate for the width of a cutting tool) or to provide an area for entering the volume defined by the virtual haptic boundary.

Once generated, the preliminary virtual haptic boundary may be registered to the patient's anatomy and displayed on display 203a, 203b of CAS system 200 (Step 640). Specifically, when the preliminary virtual haptic boundary is generated based on the relative position of the virtual implant model within the virtual coordinate space, planning software associated with CAS system 200 may be configured to map the virtual surfaces and features that define the virtual haptic boundary to the virtual coordinate space associated with the patient's anatomy. As such, the boundary surfaces associated with the virtual haptic boundary become linked to the patient's anatomy, thereby defining the areas of the patient's anatomy within which the surgical instrument is permitted to operate. By registering the virtual haptic boundary to the patient's anatomy, the preliminary virtual haptic boundary becomes virtually linked to the patient's anatomy, so that the virtual haptic boundary can be tracked (and viewed) relative to the specific movements, modifications, and adjustments in the patient's anatomy during the surgical procedure.

Figure 7:
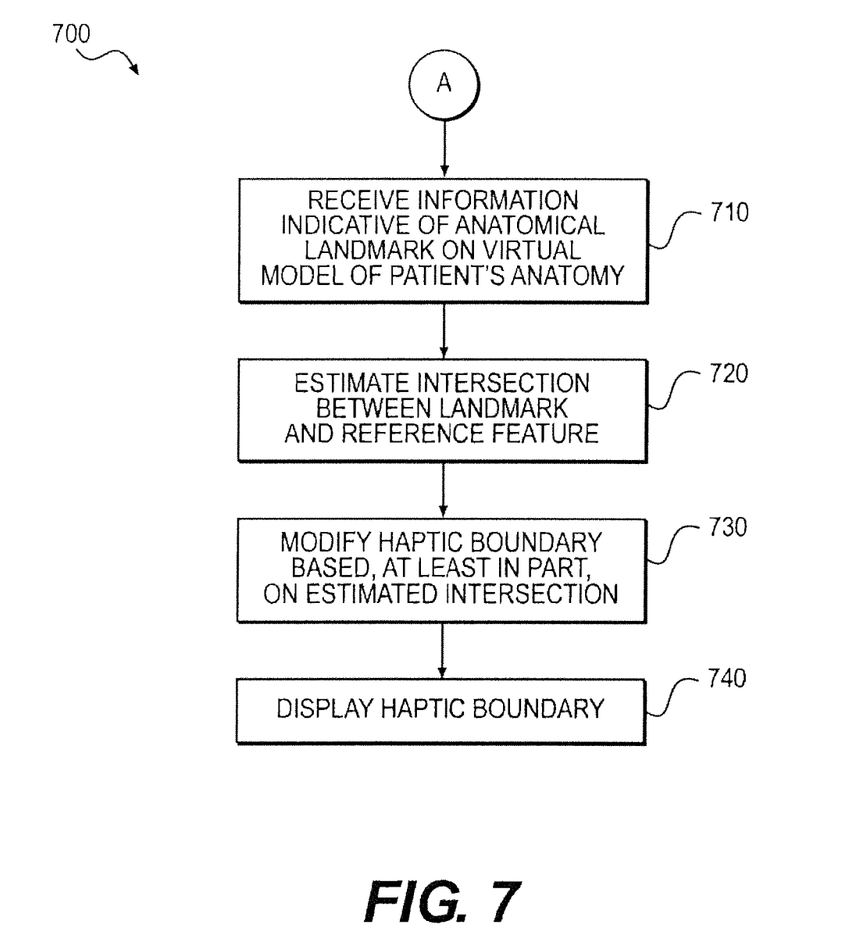
FIG. 7 provides a flowchart illustrating an exemplary method for modifying an interactive haptic boundary based on patient-specific anatomic data.

Upon displaying the preliminary virtual haptic boundary, planning software associated with CAS system 200 may be configured to allow a user to make modifications to the virtual haptic boundary to more appropriately account for certain features that are specific to the patient's anatomy. FIG. 7 provides a flowchart 700 illustrating an exemplary method for further customizing a virtual haptic boundary based, at least in part, on certain anatomic features associated with a patient. According to an exemplary embodiment, the method illustrated in FIG. 7 can be performed as an optional extension of the exemplary planning method for establishing the preliminary virtual haptic boundary illustrated in FIG. 6.

Alternatively or additionally, the method illustrated in FIG. 7 may be performed as a standalone process for modifying an established virtual haptic boundary. For example, during a pre-operative planning phase, the surgeon may develop and approve a surgical plan. As part of this pre-operative planning phase, the surgeon may establish a virtual haptic boundary associated with the pre-operative plan. Later, perhaps during a separate, intra-operative process, the surgeon may, using the process consistent with the flowchart shown in FIG. 7, modify the existing virtual haptic boundary that was previously established during the pre-operative planning phase. As a result, processes and methods consistent with the disclosed embodiments allow a user (e.g., a surgeon or other medical professional) to modify the virtual haptic boundary in real-time in order to customize the virtual boundary based on the patient-specific parameters.

As illustrated in FIG. 7, the method for customizing the virtual haptic boundary may commence upon receipt of information indicative of an anatomical landmark (or other designated feature) associated with a virtual model of the patient's anatomy (Step 710). According to one embodiment, the anatomical landmark may be automatically identified based on a geometry associated with the virtual model of the patient's anatomy. For example, planning software associated with CAS system 200 may be configured to automatically detect an anatomic feature associated with the patient's anatomy such as, for example, a perimeter of a patient's bone (e.g., tibia 101), the location of a particular protrusion associated with the patient's bone (e.g., tibial eminence 101a), or any other specific feature associated with the patient's anatomy. This feature for automatically detecting an anatomical landmark may be based on a surface analysis process performed by planning software, whereby the surface of the 3-D model associated with the patient's anatomy is scanned for surface discontinuities (e.g., a dramatic drop-off in height at the perimeter of the patient's bone) or protrusions (e.g., a dramatic increase in the surface height of the bone).

As an alternative or in addition to automatic detection, information indicative of anatomical landmarks may be received based on a user input. For example, a surgeon may designate one or more points, lines, or areas of the patient's anatomy as anatomical landmarks manually by physically touching the points, lines, or areas of the patient's anatomy using a probe tool that has been registered with the virtual coordinate space. According to another embodiment, a user of CAS system 200 may input information associated with anatomical landmarks using a graphical user interface associated with planning software. Specifically, a user may select, via a graphical user interface, one or more points, lines, surfaces, or areas on a 3-D virtual model of the patient's anatomy using a mouse or other input device.

FIG. 5 illustrates a plurality of exemplary anatomical landmarks associated with tibia 101, which may be established as part of an exemplary surgical procedure for implanting a tibial prosthetic system 120. As illustrated in FIG. 5, anatomical landmarks 510, 512 may be associated with a perimeter of tibia 101. According to one embodiment, the perimeter of tibia 101 may be established as the perimeter of the upper surface of tibia 101 (as with anatomical landmark 510). In certain embodiments, however, the perimeter of tibia 101 may be allowed to extend beyond the end of the surface of tibia 101 (as with anatomical landmark 512) to account for portions of tibia 101 that may extend laterally beyond the surface of tibia 101 (such as anatomical landmark 517).

FIG. 5 also illustrates exemplary anatomical landmarks 520, 522 that may be associated with certain protrusions associated with the patient's anatomy. As illustrated in FIG. 5, anatomical landmarks 520, 522 may correspond with areas surrounding tibial eminence 101a and/or other areas that a surgeon wishes to protect during the bone resection process.

Returning to FIG. 7, once information indicative of patient-specific anatomical landmarks has been received, the intersection between the anatomical landmark and a reference feature associated with the virtual implant model may be determined (Step 720). As explained, reference feature 505 may be designated as the plane defined by the medial and lateral base portions 121a, 121b, which ultimately define the depth of bone resection of tibia that is required to accommodate the planned placement of the tibial implant.

Planning software associated with CAS system 200 may be configured to estimate the intersection between the selected anatomical landmarks 510, 512, 520, 522 and the reference feature 505. According to one embodiment, each of intersection points 515, 517, 525, 527 may be estimated as the closest point along reference feature 505 to corresponding anatomical landmarks 510, 517, 520, 522, respectively. Alternatively or additionally, intersection points 515, 517, 525, 527 may be estimated based on the anatomical profile of the patient's anatomy. For example, intersection points 515 and 517 associated with anatomical landmarks 510 and 512 may be estimated based on the intersection between the perimeter of the bone and the reference feature 505.

Turning back to FIG. 7, upon estimating the intersection between the anatomical landmark(s) and reference feature associated with the virtual implant model, planning software associated with CAS system 200 may be configured to modify the virtual haptic boundary based, at least in part, on the estimated intersection (Step 730). According to one embodiment, the modified haptic boundary may be established by stretching (or contracting) a surface associated with the preliminary virtual haptic boundary to one or more of anatomical landmarks 510, 512, 520, 522. Planning software associated with CAS system 200 may then modify the virtual haptic boundary based on the overlap between the stretched (or contracted) surface and the virtual model of the patient's anatomy to generate a new, patient-specific virtual haptic boundary based on the overlapping area(s). CAS system 200 may then apply the virtual haptic boundary to surgical instrument, and display the modified virtual haptic boundary on display devices 203a, 203b (Step 740).

Figure 8:
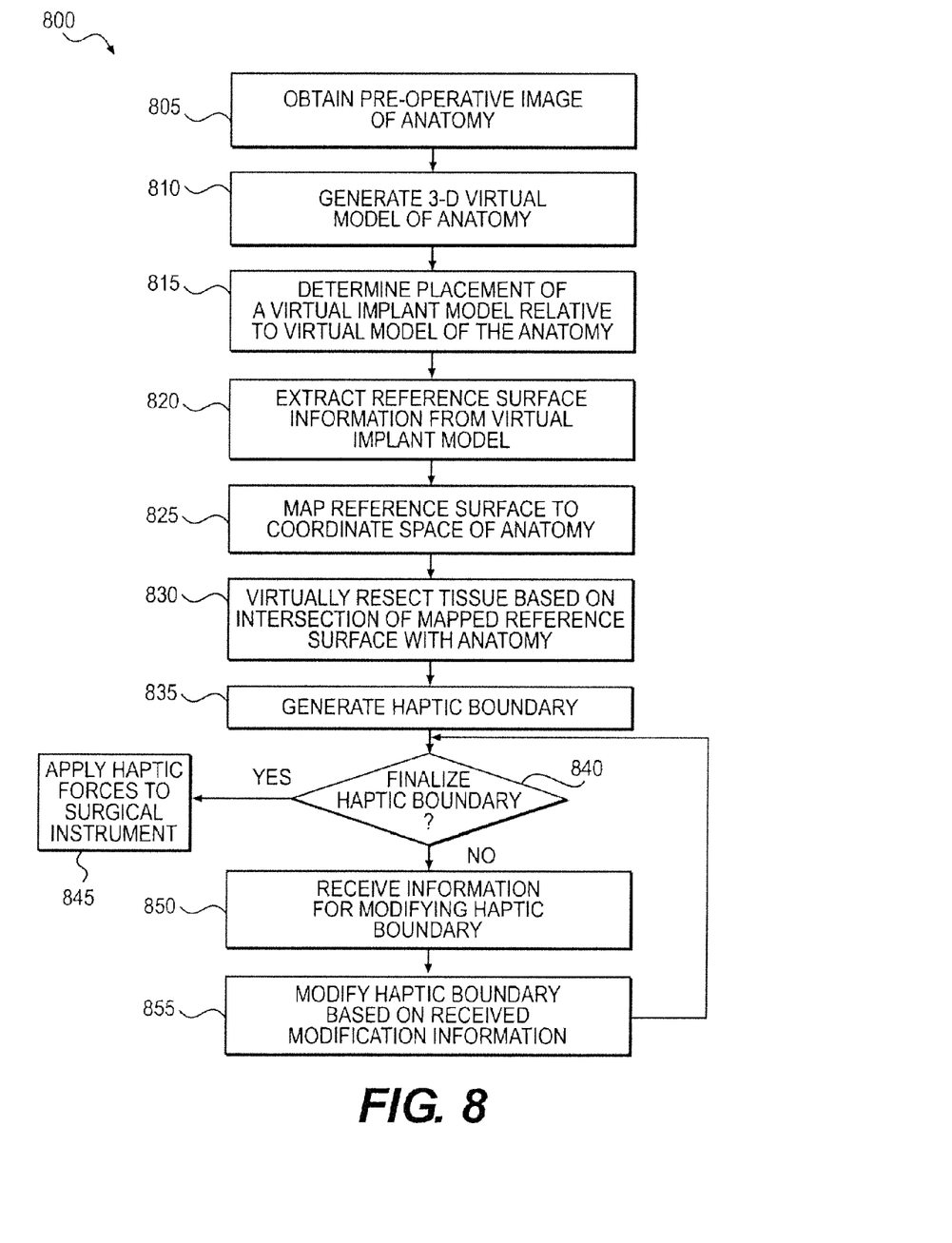
FIG. 8 provides a flowchart illustrating another exemplary method for customizing interactive haptic boundaries based on patient-specific data.

FIG. 8 provides a flowchart 800 showing another exemplary method for customizing a haptic boundary based on patient-specific parameters. As illustrated in FIG. 8, the method may commence upon receipt of pre-operative image (s) or image data associated with a patient's anatomy (Step 805). Pre-operative image(s) may include any two- or three-dimensional image data set obtained using any suitable imaging process for recording images associated with a patient's anatomy such as, for example, x-ray, computed tomography (CT), magnetic resonance (MR), positron emission tomography (PET), single photon emission computed tomography (SPECT), ultrasound, etc. According to one embodiment, I/O devices 236 of CAS system 200 may receive pre-operative CT scan data 260 associated with the anatomy of the specific patient that is to be operated on.

Upon receiving pre-operative image of the anatomy of a patient, software associated with CAS system 200 may generate a 3-D virtual model of the patient's anatomy (Step 810). For example, CAS system 200 may include one of a number of different software tools for rendering 3-D models of objects, based on the received 2-D (or 3-D) image data sets associated with the anatomy of the patient. In an alternative embodiment, the 3-D virtual model of the patient's anatomy is generated utilizing an imageless system.

After the virtual model of the patient's anatomy is generated, it may be registered with the actual anatomy of the patient so that CAS system 200 can virtually track the position and orientation of the actual anatomy of the patient in virtual software space. According to one embodiment, this registration process involves associating a plurality of points of the patient's anatomy with corresponding points on the virtual model. As explained above, such associations can be made using a probe tool that has been registered in the virtual coordinate space, whereby a plurality of points on the patient's anatomy gathered by touching or "exploring" one or more surfaces of the patient's anatomy using the tip of the probe tool. Once the virtual model is registered with the patient's anatomy, CAS system 200 may be able to track the position and orientation of the patient's anatomy in the virtual coordinate space.

After the 3-D virtual model of the patient's anatomy is generated and registered to the patient's bone, planning software of CAS system 200 may be configured to facilitate the planning of an prosthetic implant within the patient's anatomy (Step 815). Specifically, planning software of CAS system 200 may be configured to determine, based on a user input, placement of a virtual implant model relative to the virtual model of the patient's anatomy. For example, a surgeon may select a virtual implant model (e.g., virtual model associated with tibial base portion 121 as shown in FIG. 4) from a database of implants available for the surgery. Using a graphical user interface 400, the surgeon may manipulate the position of the virtual implant model relative to the patient's anatomy (e.g., tibia 101), which produces a virtual representation of the tibia fitted with the virtual implant, as shown in the lower left sub-screen of graphical user interface 400 of FIG. 4. Such a process for virtually planning implant placement allows the surgeon to make precise adjustments to the position of the implant relative to the patient's anatomy in a simulated software environment, prior to commencing the bone resection process.

Once the placement of the virtual implant model with respect to the virtual model of the patient's anatomy is finalized, the reference surface information may be extracted from the virtual implant model (Step 820). According to one embodiment, the reference surface of the virtual implant model may embody one or more points, lines, planes, or surfaces of the virtual implant model. As illustrated in the embodiment illustrated in FIG. 5, the reference feature may be a reference plane 505 defined by the bottom surfaces of medial and lateral base portions 121a, 121b of a base portion 121 of tibial implant system 120. Alternatively or additionally, the reference surface may include or embody any feature associated with the implant that the surgeon wishes to use as the reference with which to customize virtual haptic boundaries. For example, reference surface may include any surface associated with the virtual implant model that directly abuts or faces a surface of the virtual model associated with the patient's anatomy.

Upon extracting the reference surface information, planning software associated with CAS system 200 may map the reference surface information onto the coordinate space of the patient's anatomy (Step 825). That is, planning software associated with CAS system 200 may register the reference surfaces of the virtual implant model to the virtual model of the patient's bone, such that the reference surfaces are tracked relative to the position of the patient's bone.

Planning software of CAS system 200 may be configured to determine the intersection between the mapped reference surface and the patient's anatomy, and virtually resect tissue based on the determined intersection (Step 830). The lower right-hand sub-screen of graphical user interface 400 of FIG. 4 illustrates respective medial and lateral resection portions 401a, 401b of the patient's bone that have been resected based on the intersection between the reference surface of the virtual implant model and the virtual model associated with the patient's anatomy. As illustrated in FIG. 4, the implant-specific reference surface has been transferred to the patient-specific anatomical model and, based on the intersection between the two surfaces, the patient-specific resection region associated with the generic implant model may be identified.

Planning software of CAS system 200 may also be configured to generate a preliminary virtual haptic boundary based on the intersection between the reference surface associated with the virtual implant model and the virtual model of the patient's anatomy (Step 835). For example, upon identifying the overlapping volume between the reference surfaces of virtual implant model and the virtual model of the patient's anatomy, planning software of CAS system 200 may be configured to generate a virtual haptic boundary based, at least in part, on the identified overlapping volume. This preliminary virtual haptic boundary typically corresponds closely with the geometric shape of the prosthetic implant. According to some embodiments, however, it may differ slightly from the geometry of the implant. For example, the preliminary virtual haptic boundary may be slightly larger than the prosthetic implant to allow sufficient space for surgical tool access (e.g., to accommodate for the width of a cutting tool) or to provide an area for entering the volume defined by the virtual haptic boundary.

Upon generating the preliminary virtual haptic boundary, planning software of CAS system 200 may provide the user with an option to finalize the virtual haptic boundary (Step 840). If the user decides to finalize the virtual haptic boundary (Step 840:Yes), CAS system 200 may update the force system with the coordinates of virtual haptic boundary. As such, CAS system 200 may be configured to selectively apply the virtual haptic forces to surgical instrument based on the tracked position of the surgical instrument relative to the virtual haptic boundary (Step 845).

If, on the other hand, the user elects instead to modify the virtual haptic boundary (Step 840: No), planning software of CAS system 200 may receive information for modifying the virtual haptic boundary (Step 850). Information for modifying the virtual haptic boundary may be received automatically (based on a particular anatomic feature), manually (based on a user input for modifying the boundary), or a combination of both automatic and manual methods.

For example, planning software associated with CAS system 200 may be configured to automatically detect an anatomic feature associated with the patient's anatomy such as, for example, a perimeter of a patient's bone (e.g., tibia 101), the location of a particular protrusion associated with the patient's bone (e.g., tibial eminence 101a), or any other specific feature associated with the patient's anatomy. This feature for automatically detecting an anatomical landmark may be based on a surface analysis process performed by planning software, whereby the surface of the 3-D model associated with the patient's anatomy is scanned for surface discontinuities (e.g., a dramatic drop-off in height at the perimeter of the patient's bone) or protrusions (e.g., a dramatic increase in the surface height of the bone).

As an alternative or in addition to automatic detection, information indicative of anatomical landmarks may be received based on a user input. For example, a surgeon may designate one or more points, lines, or areas of the patient's anatomy as anatomical landmarks manually by physically touching the points, lines, or areas of the patient's anatomy using a probe tool that has been registered with the virtual coordinate space. According to another embodiment, a user of CAS system 200 may input information associated with anatomical landmarks using a graphical user interface associated with planning software. Specifically, a user may select, via a graphical user interface, one or more points, lines, surfaces, or areas on a 3-D virtual model of the patient's anatomy using a mouse or other input device.

Based on the received information, planning software associated with CAS system 200 may be configured to modify the virtual haptic boundary based, for example, on the estimated intersection between the anatomical landmarks and the reference feature (Step 855). Using FIG. 5 as an example, the modified haptic boundary may be established by stretching (or contracting) a surface associated with the preliminary virtual haptic boundary (which may be associated with the geometry of a virtual implant) to one or more of anatomical landmarks 510, 512, 520, 522. Planning software associated with CAS system 200 may then modify the virtual haptic boundary based on the overlap between the stretched (or contracted) surface and the patient's anatomy to generate a new, patient-specific virtual haptic boundary based on the overlapping area(s).

The presently disclosed systems and methods for customizing virtual haptic boundaries provide a solution for easily adjusting virtual haptic boundaries associated with force feedback control system for computer-assisted surgery systems. According to one embodiment, this solution allows a user to easily modify a haptic boundary by stretching or contracting an existing haptic boundary to fit one or more anatomical landmarks. The planning software may then determine an intersection between the stretched (or contracted) boundary and the virtual model of the patient's anatomy to define the location of the new virtual haptic boundary, and establish the new virtual haptic boundary based on the determined intersection.

The foregoing descriptions have been presented for purposes of illustration and description. They are not exhaustive and do not limit the disclosed embodiments to the precise form disclosed. Modifications and variations are possible in light of the above teachings or may be acquired from practicing the disclosed embodiments. For example, the described implementation includes software, but the disclosed embodiments may be implemented as a combination of hardware and software or in firmware. Examples of hardware include computing or processing systems, including personal computers, servers, laptops, mainframes, microprocessors, and the like. Additionally, although disclosed aspects are described as being stored in a memory, one skilled in the art will appreciate that these aspects can also be stored on other types of computer-readable storage devices, such as secondary storage devices, like hard disks, floppy disks, a CD-ROM, USB media, DVD, or other forms of RAM or ROM.

It will be apparent to those skilled in the art that various modifications and variations can be made to the disclosed systems and associated methods for customizing interactive haptic boundaries based on patient-specific data. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:

1. A method for customizing an interactive haptic boundary based on a patient-specific feature, comprising:
   identifying a reference feature associated with a virtual implant model;
   determining an intersection between the identified reference feature and a virtual model associated with an anatomy of the patient; and
   generating a virtual haptic boundary based on the determined intersection between the identified reference feature associated with the virtual implant model and the virtual model associated with the anatomy of the patient.

2. The method of claim 1, further including displaying the generated virtual haptic boundary, the virtual model associated with the anatomy of the patient, and the virtual implant model on a display.

3. The method of claim 1, wherein the virtual implant model includes a virtual model of a tibial prosthetic base, wherein the reference feature includes a bottom surface of the tibial prosthetic base.

4. The method of claim 1, wherein determining the intersection between the identified reference feature and the virtual model includes:
   identifying an anatomic feature of the patient's anatomy on the virtual model;
   estimating an intersection between the reference feature associated with the virtual implant model and the anatomic feature on the virtual model; and
   generating the virtual haptic boundary based on the estimated intersection between the reference feature and the anatomic feature.

5. The method of claim 1, wherein the virtual implant model corresponds with a prosthetic implant and the reference feature associated with the virtual implant model comprises a three-dimensional virtual representation of the surface of the prosthetic implant that abuts the patient's anatomy.

6. The method of claim 1, wherein generating the virtual haptic boundary comprises:
   identifying an area of the virtual model associated with the patient's anatomy that overlaps with an area associated with the virtual implant model; and
   virtually resecting the determined overlapping area of the virtual model.

7. The method of claim 1, further comprising:
   receiving a signal indicative of a user-defined modification to the generated virtual haptic boundary; and
   modifying the generated virtual haptic boundary based on the received signal.

8. The method of claim 1, further comprising:
   receiving computed tomography (CT) data associated with the patient's anatomy; and
   generating the virtual model associated with the patient's anatomy based on the CT data.

9. The method of claim 1, further comprising:
   generating the virtual model associated with the patient's anatomy utilizing an imageless system.

10. The method of claim 1, further comprising:
    displaying a graphical representation of an implant in virtual coordinate space;
    displaying a graphical representation of a bone in virtual coordinate space;

positioning the graphical representation of the implant relative to the graphical representation of the bone based on a user input;

extracting reference feature information associated with the virtual representation of the implant;

mapping the extracted reference feature information to the graphical representation of the bone;

receiving information indicative of a positional landmark associated with the bone;

estimating an intersection between the positional landmark and the mapped reference feature; and generating the virtual haptic boundary based, at least in part, on the estimated intersection between the positional landmark and the mapped reference feature.

11. The method of claim 10, wherein the reference feature information includes a position and orientation of a surface of the graphical representation of the implant that abuts the graphical representation of the bone.

12. The method of claim 11, wherein the surface includes the bottom surface of the graphical representation of the implant.

13. The method of claim 12, wherein the positional landmark includes a perimeter of the bone and estimating the intersection includes calculating the intersection between the perimeter of the bone and the bottom surface of the graphical representation of the implant.

14. The method of claim 12, wherein the positional landmark includes a user-defined landmark for adjusting the virtual haptic boundary.

15. The method of claim 10, wherein generating the virtual haptic boundary includes:
retrieving a default virtual haptic boundary corresponding to the geometry of the graphical representation of the implant;
determining a difference between a position of a portion of the default virtual haptic boundary and the positional landmark associated with the bone; and
generating a modified haptic boundary based, at least in part, on the determined difference between the position of the portion of the default virtual haptic boundary and the positional landmark associated with the bone.

16. The method of claim 10, further comprising:
receiving information indicative of a numerical offset based on a user input; and
generating a modified haptic boundary based, at least in part, on the received numerical offset information.

17. A computer-assisted surgery system comprising:
a display;
an input device configured to receive data input by a user;
a processor, operatively coupled to the input device and the display and configured to:
identify a reference feature associated with a virtual implant model;
determine an intersection between the identified reference feature and a virtual model associated with an anatomy of the patient;
generate a virtual haptic boundary based on the determined intersection between the identified reference feature associated with the virtual implant model and the virtual model associated with the anatomy of the patient; and
display the generated virtual haptic boundary and the virtual model associated with the anatomy of the patient on the display.

18. The computer assisted surgery system of claim 17, wherein the processor is further configured to display the virtual implant model on the display.

19. The computer assisted surgery system of claim 17, wherein the virtual implant model includes a virtual model of a tibial prosthetic base, wherein the reference feature includes a bottom surface of the tibial prosthetic base.

20. The computer assisted surgery system of claim 17, wherein determining the intersection between the identified reference feature and the virtual model includes:
identifying an anatomic feature of the patient's anatomy on the virtual model;
estimating an intersection between the reference feature associated with the virtual implant model and the anatomic feature on the virtual model; and
generating the virtual haptic boundary based on the estimated intersection between the reference feature and the anatomic feature.

21. The computer assisted surgery system claim 17, wherein the virtual implant model corresponds with a prosthetic implant and the reference feature associated with the virtual implant model comprises a three-dimensional virtual representation of the surface of the prosthetic implant that abuts the patient's anatomy.

22. The computer assisted surgery system of claim 17, wherein generating the virtual haptic boundary comprises:
identifying an area of the virtual model associated with the patient's anatomy that overlaps with an area associated with the virtual implant model; and
virtually resecting the determined overlapping area of the virtual model.

23. The computer assisted surgery system of claim 17, wherein the processor is further configured to:
receive a signal indicative of a user-defined modification to the generated virtual haptic boundary; and
modify the generated virtual haptic boundary based on the received signal.

24. The computer assisted surgery system of claim 17, wherein the processor is further configured to:
receive computed tomography (CT) data associated with the patient's anatomy; and
generate the virtual model associated with the patient's anatomy based on the CT data.

25. The computer assisted surgery system of claim 17, wherein the processor is further configured to:
generate the virtual model associated with the patient's anatomy utilizing an imageless system.

* * * * *